United States Patent [19]

Petty

[11] Patent Number: 5,115,958
[45] Date of Patent: May 26, 1992

[54] HEMOSTATIC SURGICAL INSTRUMENT COMPRISING STAPLER AND STAPLER COMBINED WITH SURGICAL SCALPEL

[76] Inventor: Paul M. Petty, 1911 Val Kyrie Dr., NW., Rochester, Minn. 55901

[21] Appl. No.: 610,848

[22] Filed: Nov. 8, 1990

[51] Int. Cl.⁵ .............. A61B 17/068; A61B 17/32; B25C 5/00
[52] U.S. Cl. .............. 227/180; 227/19; 227/76; 227/111; 227/176; 30/294; 606/172
[58] Field of Search ............ 227/180, 19, 21, 76, 227/901, 110, 111, 28, 143, 144, 146, 176; 30/288, 294, 290, 289; 606/167, 172

[56] References Cited

U.S. PATENT DOCUMENTS

| | | | |
|---|---|---|---|
| 2,098,123 | 11/1937 | Wood | 30/294 X |
| 2,398,979 | 4/1946 | Vaughan, Jr. | 30/289 X |
| 3,586,231 | 6/1971 | Wilson | 227/111 |
| 4,244,372 | 1/1981 | Kapitanov et al. | 227/152 |
| 4,314,559 | 2/1982 | Allen | 606/45 |
| 4,520,817 | 6/1985 | Green | 227/19 |
| 4,596,351 | 6/1986 | Fedotov et al. | 227/19 |
| 4,608,981 | 9/1986 | Rothfuss et al. | 227/19 |
| 4,633,874 | 1/1987 | Chow et al. | 227/19 |

OTHER PUBLICATIONS

Orticochea, Brit. J. Plast. Surg. 30:223 (1977).
Hammersley, J. Oral Maxillofacial Surg. 41:686 (1983).
Coleman et al., Surg. Gynecol. Obstet. 166:165 (1988).
Sakhai, J. Neurosurg. 70:142 (Tech. Note) (1989).
Sykes et al., Ann. Emerg. Med. 18:995 (1989).

Primary Examiner—Douglas D. Watts
Assistant Examiner—C. Dexter
Attorney, Agent, or Firm—Patterson & Keough

[57] ABSTRACT

The hemostatic surgical instrument comprises a scalpel provided at its anterior end with an upwardly directed surgical blade. A unique guidance means, or plow-like structure, is connected to the anterior end of the scalpel, immediately beneath the surgical blade. The plow-like structure allows the scalpel to be positioned at an appropriate depth and location with respect to individual tissue layers during formation of an incision. The instrument further comprises a stapling device with curved edges that may be used in conjunction with the scalpel to provide for placement of rows of surgical staples on either side of an incision as the incision is formed, thereby minimizing bleeding. The stapling device preferably is composed of wheels pivotally connected with the scalpel, the wheels being rollable along the surface of the tissue and capable of sequentially ejecting staples on either side of an incision as the incision is formed by the scalpel. The curved edges of the stapling device allow the instrument to be readily used for making incisions in tissues with complex curvature, such as would be encountered with pericranial incisions.

27 Claims, 6 Drawing Sheets

HEMOSTATIC SURGICAL INSTRUMENT COMPRISING STAPLER AND STAPLER COMBINED WITH SURGICAL SCALPEL

BACKGROUND OF THE INVENTION

1. Field of the Invention

This invention relates to a hemostatic surgical instrument. More specifically, this invention relates to a surgical scalpel with guide means to facilitate appropriate placement during formation of an incision, for example between the pericranium and galea of the scalp. The invention also relates to a surgical stapling device with convex outer margin, which device may be combined with the surgical scalpel, allowing placement of parallel rows of staples on either side of an incision with minimal blood loss.

2. Background Information

With standard methods, incisions through the scalp involve a substantial blood loss both at the initiation and at the end of the procedure. In general, the scalp is a very vascular entity with a large plexus of blood vessels within the galeal layer. The standard method for incising the scalp at this time involves making an initial incision with a standard scalpel followed by the placement of hemostatic clips, one form of which is commonly referred to in the art as the Raney clip. Because of the time involved and the profuse bleeding from cranial blood vessels, loss of blood is of major concern in these procedures. See, for example, Ortichochea, *A Pneumatic Cranial Tourniquet to Control Haemorrhage During Operations on the Scalp*, 30 British J. Plastic Surg., 223-26 (1977); Hammersley, *Clips for the Control of Hemorrhage from the Bitemporal Scalp Flap*, 41 J. Oral Maxillofac. Surg. 686-87 (1983); Coleman & Rocko, *Rapid Control of Hemorrhage of the Scalp in the Patient with Trauma*, 166 Surg., Gynecol. & Obstetrics 165-66 (1988); Sakhai, *Hemostatic Control of Scalp Incisions*, 70 J. Neurosurg. 142 (1989), incorporated herein in their entirety by reference thereto. There is a significant blood loss between initial formation of the incision and placement of the hemostatic clips at the beginning of the case and another period of blood loss between the time the clips are removed and the scalp is closed at the end of the case. This blood loss is frequently in the range of an entire unit of blood.

Several hundred thousand pericranial incisions are done in North America, South America, Japan, and Europe on a yearly basis. The threat of hepatitis and AIDS with blood transfusions is a significant incentive to use any instrument that significantly decreases the need for blood transfusions.

Other surgical instruments encompass surgical stapling units, or surgical stapling units in conjunction with surgical blades, allowing formation of an incision with concurrent placement of surgical staples on either side of the incision. Such instruments are exemplified by Kapitanov et al. U.S. Pat. No. 4,244,372, Green U.S. Pat. No. 4,520,817, Fedotov et al. U.S. Pat. No. 4,596,351, Rothfuss et al. U.S. Pat. No. 4,608,981, and Chow et al. U.S. Pat. No. 4,633,874. However, none of these instruments is readily adaptable to performing incisions on the surfaces of curved tissue substrates, such as the scalp, by providing for a curved stapling unit capable of following complex curvatures in multiple planes. In addition, none of the above instruments specifically provides for guide means to define an interval between specific tissue layers, for example between the galea and pericranium during a scalp incision.

Accordingly, there is a need for an instrument designed to make an incision in a tissue of complex curvature with minimal blood loss and to allow closure prior to removing the hemostatic element. A further need exists for an instrument that will significantly reduce the operating time for surguries involving pericranial incisions in both neurosurgery and plastic surgery, and thus result in a corresponding reduction in blood transfusions and the costs and dangers associated therewith.

SUMMARY OF THE INVENTION

The invention provides a hemostatic surgical instrument designed to provide an incision of defined depth and to allow placement of surgical staples, preferably in conjunction with formation of the incision, for minimizing blood loss during surgical procedures on curved tissue substrates.

The invention comprises a surgical scalpel having a handle end and an opposite anterior, or blade, end supporting an upwardly directed knife blade. A unique guidance means, or plow member, is connected with the blade end and is positioned beneath the blade to facilitate positioning of the scalpel during formation of an incision by the scalpel. In a preferred embodiment, the plow member is a generally flat, triangular-shaped platform with its apex pointed anteriorly and with its lateral surfaces extending outwardly in opposite directions from the blade end of the scalpel. The plow member is connected with the blade end of the scalpel at a point approximately mid-way between the upper right and upper left lateral surfaces of the plow member. For use in scalp incisions, it is preferred that the plow member be canted with respect to the long axis of the scalpel. It is also preferred that the leading, or anterior-most edge of the plow member be composed of a material having a low coefficient of friction, such as teflon, to facilitate movement of the plow member through the tissue being incised.

The invention also comprises a surgical stapling device. The stapling device comprises a stapling member with a convex edge portion. The rounded nature of this edge portion allows the stapling member to be rolled along its edge by any means appropriate for causing rolling movement. Surgical staples disposed within the stapling member are sequentially placed within the adjacent body tissue. This is accomplished by appropriate means within the stapling member for ejecting staples outwardly into the adjacent body tissue as the stapling member is rolled along its edge portion. The result is a row of surgical staples situated within the body tissue.

The convex edge portion of the stapling member may subtend an arc having a constant radius. In the most preferred embodiment, the stapling member comprises a rollable wheel having a hub and peripheral structure, with the surgical staples housed within the peripheral structure. In this embodiment, the means for causing rolling movement comprises a handle connected with the hub for rotation of the peripheral structure about an axis of rotation independently of the handle.

The means for sequentially ejecting the staples may comprise a cam device, disposed within the stapling member, for advancing the staples outwardly from the peripheral structure of the wheel into the adjacent body tissue as the wheel is rolled. In an alternative embodiment, a spring-biased mechanism may be used to eject the staples. For example, each staple may be spring loaded, and each staple may have a lever mechanism operationally engaged as each staple is put into position over the body tissue, leading to trip-firing of the staple by release of the spring with concomitant ejection of the staple outwardly into the adjacent body tissue. In a further alternative embodiment, the staples may be ejected by manual operation of a lever operationally engaging means for ejecting each staple as the staple is brought into position over the adjacent body tissue. In a further alternative embodiment, the staples may be ejected by use of pressurized gas under containment within the stapling member, for imparting force to each staple as the staple is brought into position over the adjacent body tissue.

According to a further aspect of the invention, the scalpel may be used in combination with the stapling device to provide a hemostatic surgical instrument. The instrument comprises a surgical scalpel having a handle end and an opposite anterior, or blade, end supporting an upwardly directed knife blade. A unique guidance means, or plow member, is connected with the blade end and is positioned beneath the blade to facilitate positioning of the scalpel during formation of an incision by the scalpel. The instrument further comprises a stapling device comprising a pair of spaced, connected stapling members, each of the stapling members having a convex edge portion. The rounded nature of these edge portions allows the stapling member to be rolled along its edges by any means appropriate for causing rolling movement. The stapling members are positioned on opposite sides of the scalpel and in operational proximity to the knife blade and the plow member. The stapling member are pivotally connected to the scalpel, allowing for rolling movement of the stapling members along a surgical incision. More specifically, the pivotal connection of the scalpel with the stapling device allows for placement of each stapling member in operational proximity with the upper left and upper right lateral surfaces, respectively, of the plow member. Surgical staples disposed within the stapling members are sequentially placed within the adjacent body tissue. This is accomplished by appropriate means within each stapling member for ejecting staples outwardly as the stapling member is rolled along its edge portion. The staples are driven into the adjacent body tissue and onto the upper right and upper left lateral surfaces of the plow member, thereby deforming the staples and causing the staples to become anchored within the body tissue. The result is two parallel rows of surgical staples situated within the body tissue on either side of the incision formed by the knife blade.

In a preferred embodiment of the instrument, the plow member is a generally flat, triangular-shaped platform with its apex pointed anteriorly and with its lateral surfaces extending outwardly in opposite directions from the blade end of the scalpel. The plow member is connected with the blade end of the scalpel at a point approximately mid-way between the upper right and upper left lateral surfaces of the plow member. For use in scalp incisions, it is preferred that the plow member be canted with respect to the long axis of the scalpel. It is also preferred that the leading, or anterior-most edge of the plow member be composed of a material having a low coefficient of friction, such as telflon, to facilitate movement of the plow member through the tissue being incised.

The convex edge portion of each stapling member may subtend an arc having a constant radius. In the preferred embodiment of the instrument, each stapling member comprises a rollable wheel having a hub and peripheral structure, and with the surgical staples housed within the peripheral structure. In this embodiment, the means for causing rolling movement and for pivotally connecting the stapling members with the scalpel comprises a pair of arms, each of the arms pivotally connected at one end with the scalpel and at the other end with the hub of one of the stapling members, allowing for rotation of the peripheral structure of each stapling member about an axis of rotation independently of the scalpel and the arms.

The means for sequentially ejecting the staples may comprise a cam device, disposed within each stapling member, for advancing the staples outwardly from the peripheral structure of the wheel into the adjacent body tissue as the wheel is rolled. In an alternative embodiment, a spring-biased mechanism may be used to eject the staples. For example, each staple may be spring loaded, and each staple may have a lever mechanism operationally engaged as each staple is put into position over the body tissue, leading to trip-firing of the staple by release of the spring with concomitant ejection of the staple outwardly into the adjacent body tissue. In a further alternative embodiment, the staples may be ejected by manual operation of a lever operationally engaging means for ejecting each staple as the staple is brought into position over the adjacent body tissue. In a further alternative embodiment, the staples may be ejected by use of pressurized gas under containment within the stapling member, for imparting force to each staple as it is brought into position over the adjacent body tissue.

DESCRIPTION OF THE PREFERRED EMBODIMENTS

Figure 1:
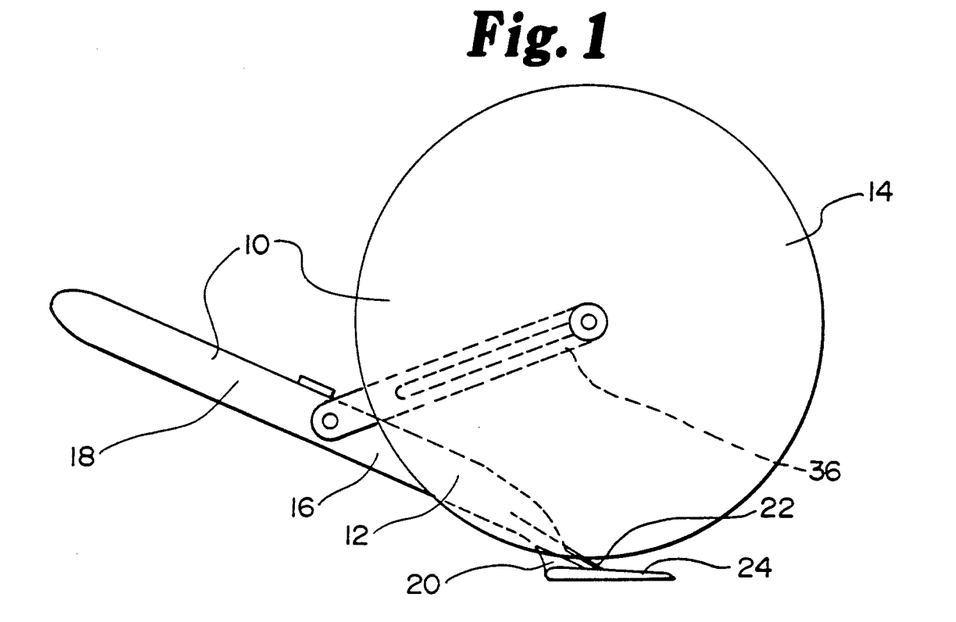
FIG. 1 is a side elevational view of the preferred embodiment of the hemostatic surgical instrument of the present invention.
Figure 2:
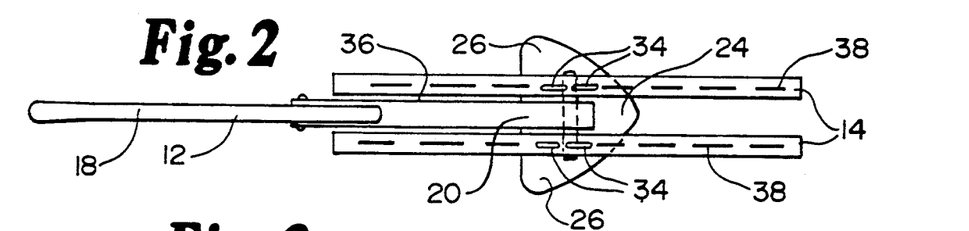
FIG. 2 is a top elevational view of the hemostatic surgical instrument shown in FIG. 1.
Figure 3:
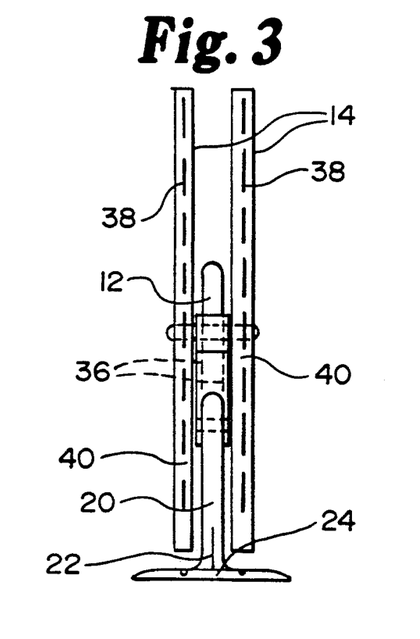
FIG. 3 is a forward end elevational view of the hemostatic surgical instrument shown in FIG. 1.
Figure 4:
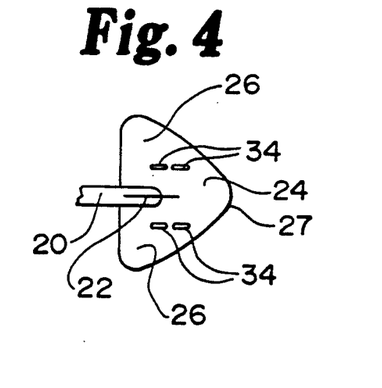
FIG. 4 is a top elevational view of the plow member, blade and anterior end of the support member of the preferred embodiment of the present invention.

Referring to the preferred embodiment shown in FIGS. 1, 2, 3 and 4, the surgical instrument 10 of the present invention comprises a scalpel 12 and a double wheel stapling unit 14. The scalpel comprises an elongate support member 16 with a handle end 18 and an opposite anterior or blade end 20. An upwardly directed surgical blade or knife blade 22 is connected with the blade end 20 of the scalpel 12, as shown in FIGS. 1, 3, and 4. Also attached to the anterior end or blade end 20 of the support member 16, and angularly disposed beneath the blade 22 is a generally triangular-shaped plow member 24, as shown in FIGS. 1, 2 and 4.

Figure 5A:
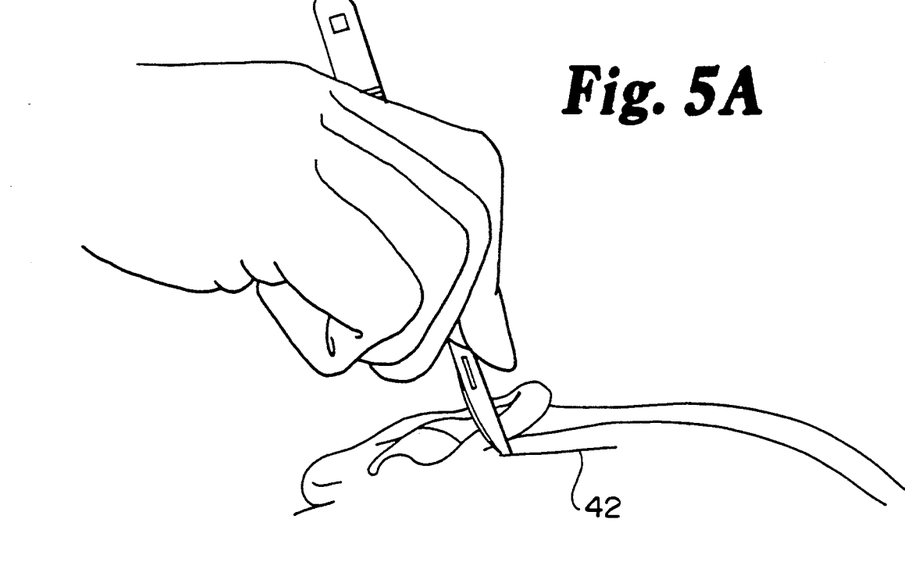
FIG. 5A is a pictorial view showing the making of an initial incision in preparation for use of the present invention.
Figure 5B:
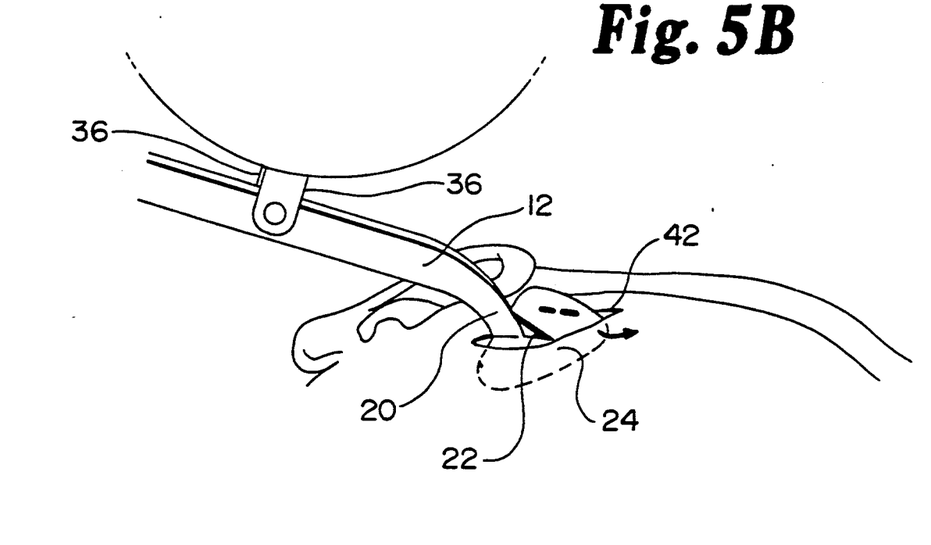
FIGS. 5B, 5C and 5D are pictorial views showing the preferred embodiment of the present invention in various stages as it is used in making a scalp incision.
Figure 5C:
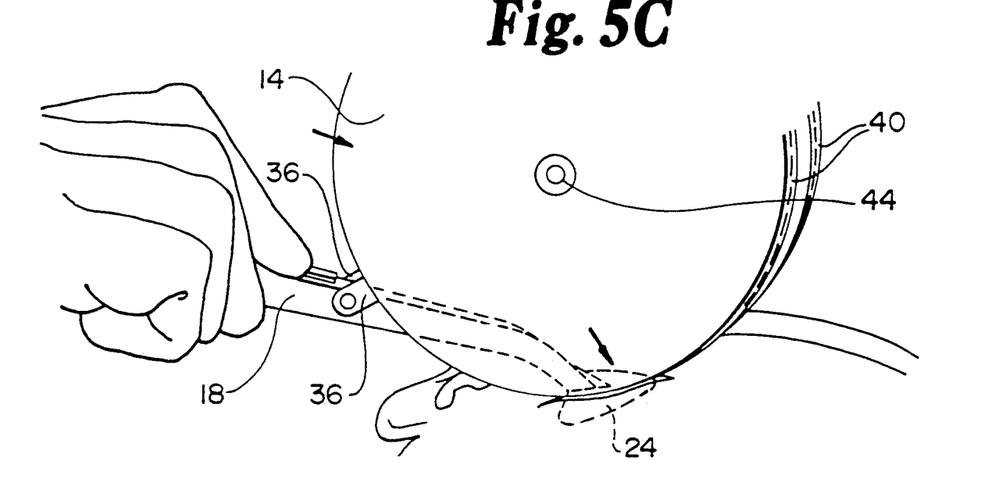

In the preferred embodiment, the plow member 24 is a flat, planar, generally triangular-shaped structure as shown in FIGS. 1, 2, 4 and 5B. To facilitate movement through tissue, it is preferred that the plow member 24 be of relatively small thickness compared to its width and length. The thickness of the plow member 24 may be tapered from the posterior region to the anterior region, as shown in FIG. 1, again to facilitate passage through or between tissue layers. The width of the plow member 24 will be such as to accommodate the placement of the staples 38 in the body tissue. Thus, the plow member 24 will be at least as wide as, or wider than, the desired separation between the rows of staples 38 on either side of the incision formed by the blade 22, as described below. Each of the lateral areas 26 of the plow member 24 also functions as an anvil portion to be used in conjunction with the stapling unit. Thus, as shown in FIG. 4 and in FIGS. 8-11, the upper lateral surfaces of the plow member may be provided with depressions 34, similar to the depressions found on the upper face of the anvil portion of a common office stapler, for causing deformation of the staples as they are ejected from the stapling unit 14. For use in scalp incisions and closure, the plow member is rigidly connected to the bottom edge of the blade end 20 of the scalpel, and is canted with respect to the long axis of the scalpel, as shown in FIGS. 1, 5B and 5C. Thus, for example, the blade end 20 of the scalpel may bend downward to meet the upper surface of the plow member 24, as shown in FIGS. 1, 5B and 5C. The acute angle formed by a plane corresponding to the top surface of the plow member 24 and the long axis of the scalpel 12 may be 25-35 degrees, as shown in FIGS. 1, 5B and 5C, or any other orientation appropriate to a particular surgical procedure. The shape, dimensions and orientation of the plow member may be varied to accommodate various uses and various tissue locations, which shapes, dimensions and orientations will be apparent to those skilled in the art.

The leading or anterior-most edge 27 of the plow member 24 may be manufactured from a substance with low coefficient of friction, such as Teflon ®, whereas the remainder of the plow member 24 may be manufactured of stainless steel or other suitable material. The scalpel may be made of a plastic, aluminum, or other suitable material. Other materials useful for manufacture of the various components of the present invention will be apparent to those skilled in the art. It is anticipated, but it is not necessary, that the instrument will be manufactured as a single-use, disposable form of surgical instrument.

Figure 5D:
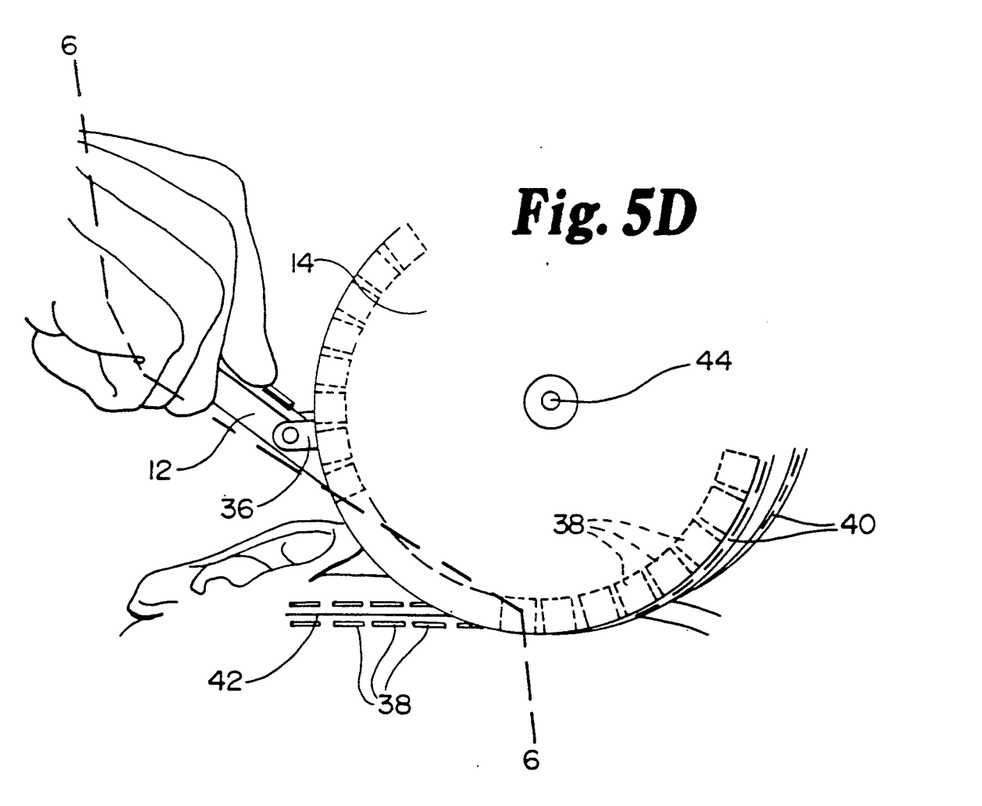

The stapling unit 14 may comprise any structure with convex outer surface subtending an arc of sufficient size to cover the desired length of pericranial incision. In the preferred embodiment, the stapling unit 14 comprises wheels 40 of approximately 35 cm circumference, which is a distance sufficient to cover a large standard pericranial incision, as shown in FIGS. 5C and 5D. Each wheel has a hub 44 allowing for rotation of the wheel 40 about an axis passing through the hub 44. Staples 38 are housed within the peripheral structure of each wheel, as shown in FIG. 5D. The staples 38 may be, for example, approximately 1 cm in width with 1 cm arms.

Although the scalpel 12 can be used by itself to form incisions of defined depth and location during cranial surgery, for example, and although the stapling unit 14 can be used by itself to control bleeding from previously formed incisions or lacerations, the preferred embodiment 10 of the present invention employs the scalpel 12 in combination with the stapling unit 14. This allows essentially simultaneous performance of the incision and stapling functions of the present invention.

In the preferred embodiment as shown in FIGS. 1-5, hinged arms 36 pivotally connect the double wheel stapling unit 14 with the handle portion 18 of the support member 16. The hinged arms 36 allow the stapling unit 14 to be rotated upwardly and away from the plow member 24 allowing for initial placement of the plow member 24 and blade end 20 of the scalpel 12 within an initial cranial incision, as shown in FIG. 5B. In operation, the stapling unit 14 is then rotated downward to place the wheels 40 on opposite sides of the blade end 20 of the scapel 12 and in operational proximity to the upper surfaces of the plow member 24, as shown in FIGS. 1, 2, 3, 5C and 6. Preferably, the pivotal connection of the hinged arms 36 with the handle portion 18 includes "stop" or "lock" positions. Thus, for example, the stapling unit 14 may be locked into operational proximity to the upper surfaces of the plow member 24 such that the pressure exerted by the stapling unit 14 on the tissue located between the stapling unit 14 and the plow member 24 is sufficient to allow effective operation of the stapling mechanism and to prevent bleeding. As a consequence of operational placement of the stapling unit 14, the knife blade 22 is located approximately midway between the bottom of each wheel 40, as shown in FIG. 3. Additionally, the wheels 40 are positioned such that the points of exit of the staples 38 from the wheels 40 are directly above the depression 34 on the upper lateral surfaces of the plow member 24, as shown in FIGS. 2, 8, 9, 10 and 11.

Figure 6:
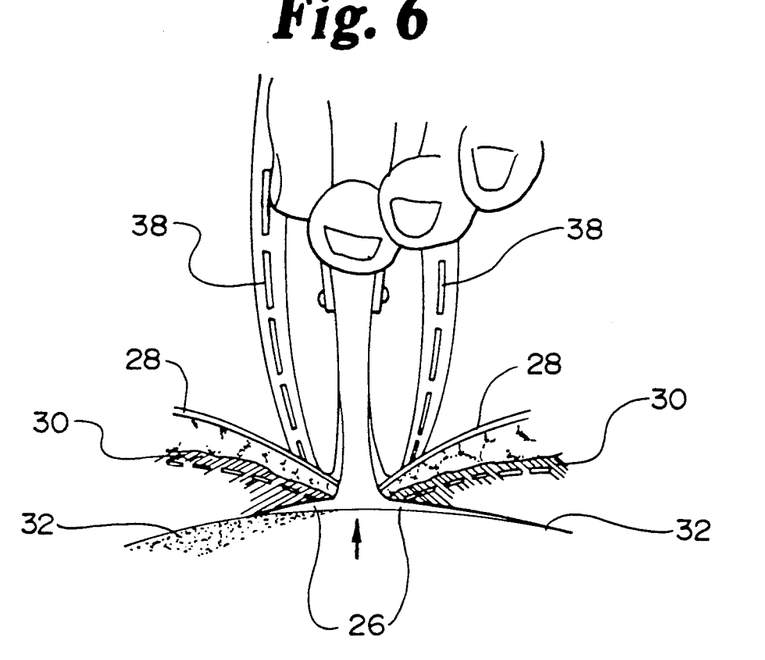
FIG. 6 is a view, partially in section, of the preferred embodiment showing placement of the plow member of the preferred embodiment between the pericranium and the galea during formation of a scalp incision, as viewed along the section line 6—6 of FIG. 5D.
Figure 7:
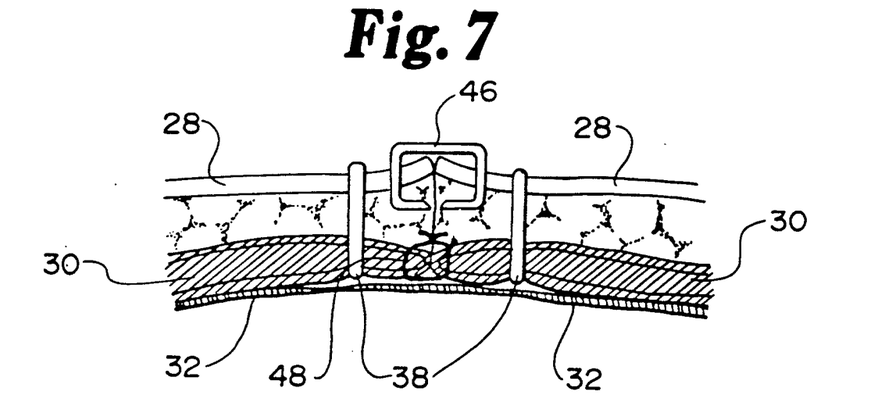
FIG. 7 is a cross-sectional view of a closed incision formed by the preferred imbodiment of the present invention, showing lateral placement of surgical staples on both sides of the incision, as well as a closure staple and suture.
Figure 8A:
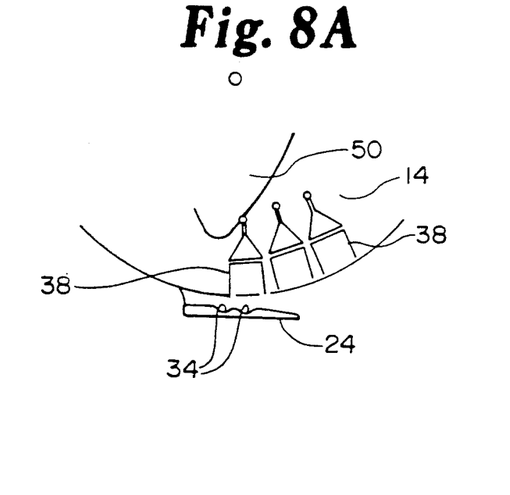
FIGS. 8A, 8B and 8C are diagramatic representations showing the operation of a cam mechanism for ejecting staples from the surgical stapling device of the present invention.
Figure 8B:
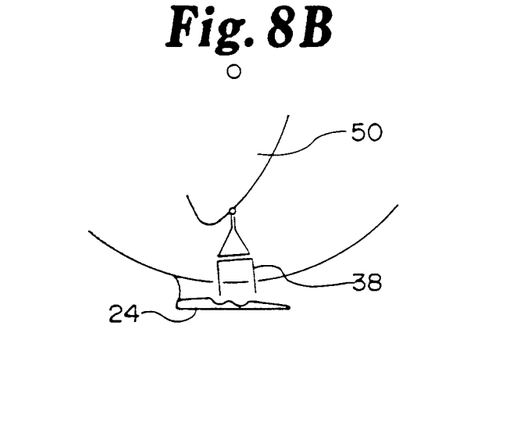
Figure 8C:
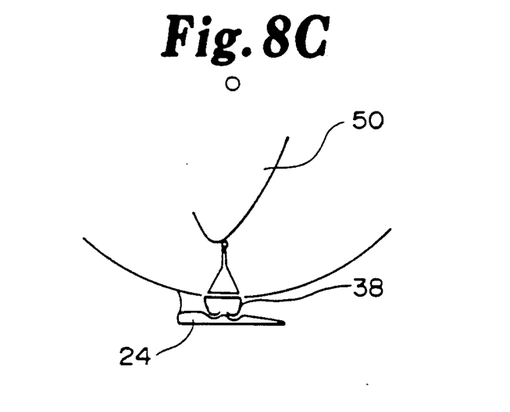
Figure 9A:
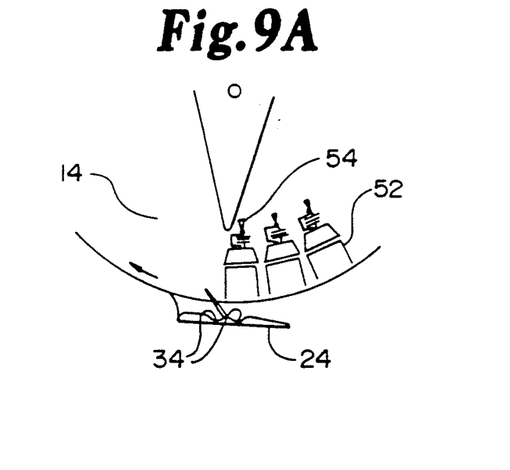
FIGS. 9A, 9B and 9C are diagramatic representations showing the operation of an alternative embodiment for ejecting staples from the surgical stapling device of the present invention, based on trip-firing of individually spring-loaded staples.
Figure 9B:
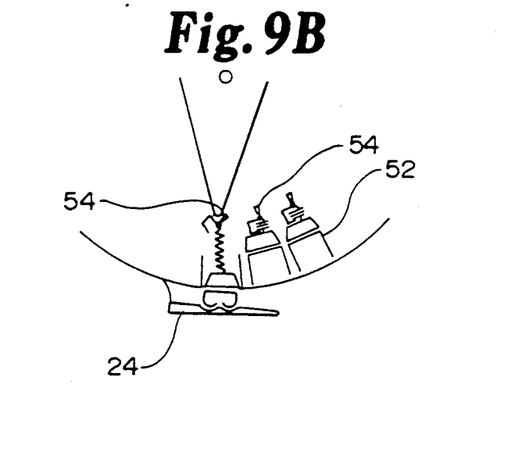
Figure 9C:
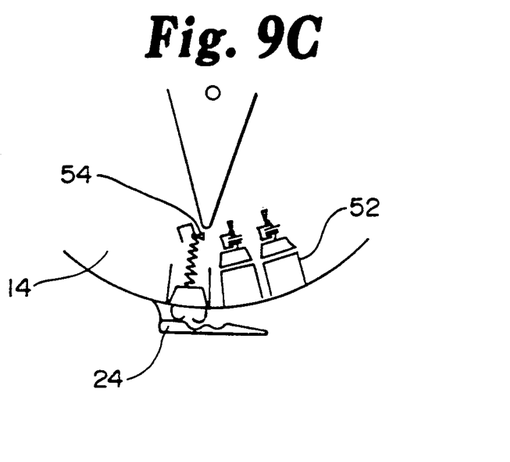
Figure 10A:
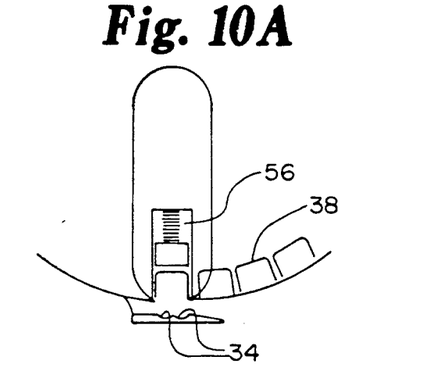
FIGS. 10A, 10B and 10C are diagramatic representations showing the operation of an alternative embodiment for ejecting staples from the surgical stapling device of the present invention, based on a manually operated lever-driven mechanism for ejecting the staples.
Figure 10B:
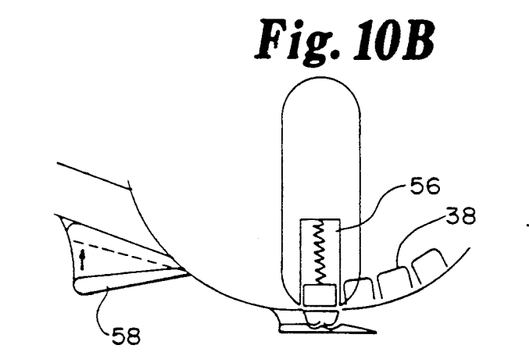
Figure 10C:
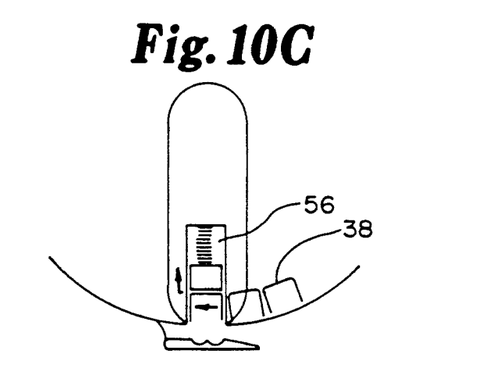

The stapling unit 14 inserts staples 38 through the skin and galea in an orientation generally parallel to the line of incision, preferably approximately 5 to 7 mm from the incision margins on each side, as shown in FIGS. 6 and 7. For incisions in the scalp, the lateral areas 26 of the plow member 24 fit below the skin 28 and galea 30 but above the pericranium 32, helping to define this region between the galea 30 and pericranium 32 and allowing formation of an incision of the desired depth as the blade 22 advances, as shown in FIGS. 6 and 7.

In typical use, the surgeon creates a small initial incision 42 in the cranial region with a standard scalpel, as shown in FIG. 5A. The blade end 20 of the scalpel with plow member 24 and blade 22 is then positioned within the initial incision 42, as shown in FIG. 5B. The final placement of the plow member is as described above and as shown in FIG. 6, that is, above the pericranium 32 and below the galea 30. With the scalpel 12 in place within the incision, the double wheel stapling unit 14 is pivoted into position over the upper surface of the plow member 24 and adjacent to the cranial skin to be incised, as shown in FIG. 5C. Finally, the scalpel 12 is pushed forward to cause lengthening of the initial incision 42 as the blade 22 is moved through the cranial skin. At the same time, the stapling unit 14 is thereby caused to rotate about its hub 44, with simultaneous engagement of a mechanism for sequentially ejecting staples from the stapling unit 14 through the skin and onto the upper lateral surfaces of the plow member 24. This forms two parallel rows of staples 38 on either side of the incision, positioned as shown in FIGS. 5D and 7. In operation, the leading edge of the blade 22 may be located just posterior to the point of entry of the staples 38 into the skin so as to allow placement of the hemostatic staples 38 prior to carrying the incision through the soft tissue layers.

Essentially bloodless scalp closure may be accomplished prior to removal of the hemostatic staples 38. For example, as shown in FIG. 7, closure staples 46 and sutures 48 may be placed independently in the skin 28 and galea 30, respectively, prior to removal of the hemostatic staples 38. Other means for accomplishing scalp closure prior to removal of the hemostatic staples will be known to those skilled in the art.

Figure 11A:
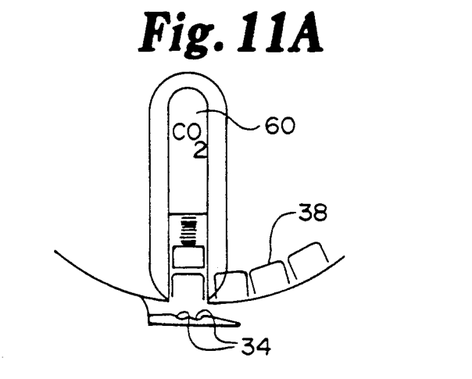
FIGS. 11A, 11B and 11C are diagramatic representations showing the operation of an alternative embodiment for ejecting staples from the surgical stapling device of the present invention, based on levered release of pressurized $CO_2$ gas for ejecting the staples.
Figure 11B:
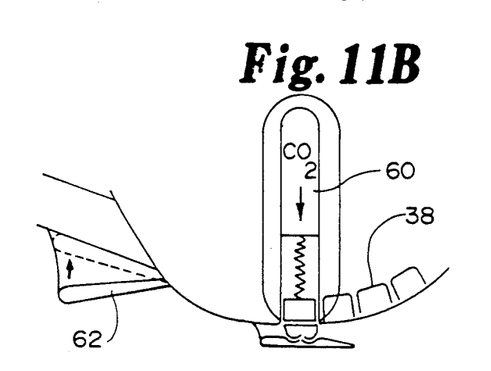
Figure 11C:
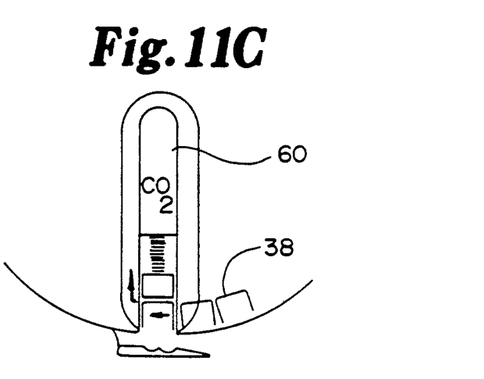

Several alternative mechanisms may be used for ejecting staples from the stapling unit. In one embodiment, a simple cam device 50 may be employed to eject the staples 38 as the stapling unit 14 is turned, as in FIG. 8. In another embodiment shown in FIG. 9, independently spring loaded staples 52 may be trip-fired by a lever mechanism 54 as each staple is put into position over the plow member 24 as the stapling unit 14 is advanced. In a further alternative embodiment shown in FIG. 10, a manually driven stapling mechanism 56 may be incorporated into the stapling unit 14. In this embodiment, manually pulling a lever 58 engages a mechanism for ejecting a staple and advancing the stapling unit to the next staple position. In still a further alternative embodiment as shown in FIG. 11, the staples may be ejected by a mechanism incorporating a container 60 of compressed gas, for example, a small cylinder of compressed carbon dioxide ($CO_2$) gas. The container 60 would be designed to provide the driving force for expelling the staples into the adjacent tissue. In this embodiment, manual operation of a lever 62 could, for example, cause sequential transient release of $CO_2$, thereby providing the necessary driving force for sequential ejection of staples as the stapling unit is advanced along the newly formed incision.

This instrument would find use in any pericranial incisions in both neurosurgery and plastic surgery. Using the instrument, an entire cranial incision procedure should take no longer than 30 seconds to one minute. It is anticipated that in numerous cases the instrument will save approximately a unit of blood loss and up to 30 minutes of operative time. The cumulative expense of blood replacement and operative time far outweigh the potential cost of this instrument.

From the foregoing, it will be apparent to those skilled in the art that various modifications in the above-described methods can be made without departing from the spirit and scope of the present invention. Present embodiments and examples, therefore, are to be considered in all respects as illustrative and not restrictive, the scope of the present invention being indicated by the appended claims rather than by the foregoing, and all changes which come within the meaning and range of equivalency of the claims are therefore intended to be embraced therein.

I claim:

1. A surgical stapling device for use with a staple-deforming surface, said staple-deforming surface adapted for placement beneath or within a body tissue, said stapling device comprising:
    (a) a rollable wheel having a hub and peripheral structure, said wheel presenting a convex edge portion subtending an arc of constant radius, said wheel being rollable along said edge portion;
    (b) a plurality of surgical staples disposed within said stapling device;
    (c) means for causing rolling movement of said wheel along a surgical incision; and
    (d) means for sequentially ejecting said staples outwardly from said edge portion of said stapling device into adjacent body tissue and onto said staple-deforming surface, during rolling movement of said wheel along said edge portion, thereby forming a row of anchored surgical staples situated within said body tissue;

wherein said staples are housed within said peripheral structure of said wheel.

2. The surgical stapling device of claim 1, wherein said means for causing rolling movement comprises a handle connected with said hub for rotation of said peripheral structure about an axis of rotation independently of said handle.

3. The surgical stapling device of claim 2, wherein said means for sequentially ejecting said staples comprises a cam device for advancing said staples outwardly from said peripheral structure of said wheel into said adjacent body tissue as said wheel is rolled.

4. The surgical stapling device of claim 2, wherein said means for sequentially ejecting said staples comprises a spring-biased mechanism for advancing said staples outwardly from said peripheral structure of said wheel into said adjacent body tissue as said wheel is rolled.

5. The surgical stapling device of claim 4, wherein each of said staples is independently spring-loaded, each of said staples having a lever mechanism operationally engaged as each staple is put into position over said tissue, said operational engagement leading to trip-firing of said staple by release of said spring and ejection of said staple outwardly from said peripheral structure into said tissue.

6. The surgical stapling device of claim 2, wherein said means for sequentially ejecting said staples comprises a pivotable lever connected with said stapling device and operably connected with means for driving said staples into said adjacent tissue, wherein manual operation of said lever operationally engages said means with said staples as said staples are brought into position adjacent to said tissue, for sequentially driving said staples outwardly from said peripheral structure into said tissue.

7. The surgical stapling device of claim 2, wherein said means for sequentially ejecting said staples comprises pressurized gas under containment for imparting force to said staples as each staple is brought into position over said tissue, thereby ejecting said staples outwardly from said peripheral structure into said tissue.

8. A hemostatic surgical instrument, comprising:
(a) an elongate support member having a handle end and an opposite blade end;
(b) an upwardly directed knife blade positioned near said blade end of said support member;
(c) a plow member having upper right and upper left lateral surfaces extending outwardly in opposite directions from said support member, said plow member being connected with said blade end of said support member and disposed beneath said knife blade for facilitating positioning of said scalpel during formation of an incision by said knife blade;
(d) a pair of spaced, connected stapling members, each of said stapling members having a convex edge portion and being rollable along said edge portion, said stapling members being positioned on opposite sides of said support member and in operational proximity to said knife blade and to said plow member;
(e) a plurality of surgical staples disposed within said stapling members;
(f) means for causing rolling movement of said stapling members along a surgical incision and for pivotally connecting said stapling members with said support member, for placement of said edge portions of each of said stapling members in operational proximity with said upper left and upper right lateral surfaces, respectively, of said plow member; and
(g) means for sequentially ejecting said staples, during rolling movement of said stapling members along said edge portions, outwardly from said edge portions into adjacent body tissue and onto said upper right and upper left lateral surfaces of said plow member, thereby deforming said staples and causing said staples to become anchored within said body tissue and forming two parallel rows of staples, the incision formed by said knife blade disposed between said rows.

9. The hemostatic surgical instrument of claim 8, wherein said plow member comprises a generally flat, triangular-shaped platform having upper and lower surfaces, leading and posterior edges, and an apex spaced from said upper left and upper right lateral surfaces, said apex pointed anteriorly and defining said leading edge of said plow member, said plow member connected with said support member at a region of said upper surface approximately mid-way between said upper right lateral surface and said upper left lateral surface.

10. The hemostatic surgical instrument of claim 9 wherein said plow member is canted with respect to the long axis of said support member.

11. The hemostatic surgical instrument of claim 10 wherein said leading edge is comprised of material having a low coefficient of friction.

12. The hemostatic surgical instrument of claim 11 wherein said material is teflon.

13. The hemostatic surgical instrument of claim 10, wherein each said convex edge portion subtends an arc having a constant radius.

14. The hemostatic surgical instrument of claim 13, wherein each said stapling member comprises a rollable wheel having a hub and peripheral structure.

15. The hemostatic surgical instrument of claim 14, wherein said staples are housed within said peripheral structure of each of said stapling members.

16. The hemostatic surgical instrument of claim 15, wherein said means for causing rolling movement and for pivotally connecting said stapling members with said handle comprises an arm, said arm having first and second ends, said arm being pivotally connected at said first end with said handle and being connected at said second end with said hub for rotation of said peripheral structure about an axis of rotation independently of said handle and said arm.

17. The hemostatic surgical instrument of claim 16, wherein said means for sequentially ejecting said staples comprises a cam device for advancing said staples outwardly from said peripheral structure of each of said wheels into said adjacent body tissue as each of said wheels is rolled.

18. The hemostatic surgical instrument of claim 16, wherein said means for sequentially ejecting said staples comprises a spring-biased mechanism for advancing said staples outwardly from said peripheral structure of each of said wheels into said adjacent body tissue as each of said wheels is rolled.

19. The hemostatic surgical instrument of claim 18, wherein each of said staples is independently spring-loaded, each of said staples having a lever mechanism operationally engaged as each staple is put into position over said tissue, said operational engagement leading to trip-firing of said staple by release of said spring and ejection of said staple outwardly from said peripheral structure into said tissue.

20. The hemostatic surgical instrument of claim 16, wherein said means for sequentially ejecting said staples comprises a pivotable lever connected with said surgical instrument and operably connected with means for driving said staples into said adjacent tissue, wherein manual operation of said lever operationally engages said means with said staples as said staples are brought into position adjacent to said tissue, for sequentially driving said staples outwardly from said peripheral structure into said tissue.

21. The hemostatic surgical instrument of claim 16, wherein said means for sequentially ejecting said staples comprises pressurized gas under containment for imparting force to said staples as each staple is brought into position over said tissue, thereby ejecting said staples outwardly from said peripheral structure into said tissue.

22. A surgical stapling device for use with a staple-deforming surface, said staple deforming-surface adapted for placement beneath or within a body tissue, said stapling device comprising:
(a) a stapling member icluding a convex tissue-engaging surface, said stapling member being rollable along said convex tissue-engaging surface;

(b) a plurality of surgical staples housed within said stapling member;

(c) means for causing rolling movement of said stapling member along said tissue-engaging surface; and (d) means for sequentially ejecting said staples through said convex tissue-engaging surface of said stapling member into adjacent body tissue and onto said staple-deforming surface as said stapling member is rolled along said convex tissue-engaging surface, thereby forming a row of anchored surgical staples in said body tissue.

23. The surgical stapling device of claim 22, wherein said convex tissue-engaging surface subtends an arc having a constant radius.

24. The surgical stapling device of claim 23, wherein said stapling member comprises a rollable wheel.

25. A hemostatic surgical instrument for concurrent formation of an incision and hemostatic placement of surgical staples, comprising:

(a) a surgical scalpel comprising guidance means for positioning said scalpel during formation of an incision by said scalpel, said guidance means including an upper surface adapted for deformation of said surgical staples, and a blade coupled with said guidance means;

(b) a stapling member including a convex tissue-engaging surface, said stapling member being rollable along said convex tissue-engaging surface;

(c) a plurality of surgical staples housed within said stapling member;

(d) means for pivotally mounting said stapling member on said surgical scalpel and for causing rolling movement of said stapling member along said tissue-engaging surface; and (e) means for sequentially ejecting said staples through said convex tissue-engaging surface of said stapling member into adjacent body tissue and onto said upper surface of said guidance means as said stapling member is rolled along said convex tissue-engaging surface, thereby forming a row of anchored surgical staples in said body tissue adjacent said incision.

26. A stapling device for ejection of staples into a substrate having a staple-receiving surface, comprising:

(a) a stapling member including a convex edge portion, said stapling member being rollable along said edge portion;

(b) a plurality of staples disposed within said stapling member;

(c) means for causing rolling movement of said stapling member on said surface; and (d) means for sequentially ejecting said staples through said convex edge portion into said substrate as said stapling member is rolled on said surface, thereby forming a row of staples in said substrate.

27. The stapling device of claim 26, wherein said stapling member comprises a rollable wheel.

* * * * *